US008797525B2

(12) United States Patent
Ogawa

(10) Patent No.: US 8,797,525 B2
(45) Date of Patent: Aug. 5, 2014

(54) PATTERN INSPECTION APPARATUS AND PATTERN INSPECTION METHOD

(75) Inventor: Riki Ogawa, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 0 days.

(21) Appl. No.: 13/608,026

(22) Filed: Sep. 10, 2012

(65) Prior Publication Data

US 2013/0083318 A1    Apr. 4, 2013

(30) Foreign Application Priority Data

Sep. 29, 2011    (JP) .................................. 2011-214273

(51) Int. Cl.
*G01N 21/956* (2006.01)
(52) U.S. Cl.
CPC .................................. *G01N 21/956* (2013.01)
USPC .................. 356/237.5; 356/237.1; 356/237.2; 356/237.3; 356/237.4
(58) Field of Classification Search
CPC .................................................. G01N 21/956
USPC .................... 356/237.1–237.5; 355/67, 68, 53
See application file for complete search history.

(56) References Cited

U.S. PATENT DOCUMENTS

| | | | | |
|---|---|---|---|---|
| 3,988,066 A | * | 10/1976 | Suzuki et al. | 355/78 |
| 5,170,063 A | * | 12/1992 | Miyazaki et al. | 250/559.45 |
| 5,420,417 A | * | 5/1995 | Shiraishi | 250/205 |
| 5,991,009 A | * | 11/1999 | Nishi et al. | 355/70 |
| 6,049,374 A | * | 4/2000 | Komatsuda et al. | 355/67 |
| 6,819,414 B1 | * | 11/2004 | Takeuchi | 356/124 |
| 6,927,836 B2 | * | 8/2005 | Nishinaga | 355/53 |
| 7,345,755 B2 | * | 3/2008 | Ogawa et al. | 356/237.5 |
| 7,698,000 B2 | * | 4/2010 | Silberberg et al. | 700/1 |
| 2002/0001759 A1 | * | 1/2002 | Ohashi et al. | 430/5 |
| 2006/0257756 A1 | * | 11/2006 | Ohashi et al. | 430/5 |
| 2007/0058274 A1 | * | 3/2007 | Singer et al. | 359/857 |
| 2007/0103893 A1 | * | 5/2007 | Tanaka | 362/138 |
| 2007/0252968 A1 | * | 11/2007 | Ohkubo et al. | 355/67 |
| 2009/0073430 A1 | * | 3/2009 | Iwase | 356/237.5 |
| 2009/0244531 A1 | * | 10/2009 | Takada | 356/237.5 |
| 2010/0321680 A1 | * | 12/2010 | Takada | 356/237.5 |

FOREIGN PATENT DOCUMENTS

JP    2011-53120    3/2011

* cited by examiner

*Primary Examiner* — Sang Nguyen
(74) *Attorney, Agent, or Firm* — Oblon, Spivak, McClelland, Maier & Neustadt, L.L.P.

(57) ABSTRACT

A pattern inspection apparatus in accordance with one aspect of the present invention includes a laser light source configured to emit a laser light, an integrator lens configured to input the laser light, and form a light source group by dividing the laser light inputted, a scattering plate, arranged at a front side of an incident surface of the integrator lens, configured to scatter the laser light which is to enter the integrator lens, and an inspection unit configured to inspect a defect of a pattern on an inspection target object where a plurality of figure patterns are formed, by using the laser light having passed through the integrator lens as an illumination light.

20 Claims, 7 Drawing Sheets

PATTERN INSPECTION APPARATUS AND PATTERN INSPECTION METHOD

CROSS-REFERENCE TO RELATED APPLICATION

This application is based upon and claims the benefit of priority from the prior Japanese Patent Application No. 2011-214273 filed on Sep. 29, 2011 in Japan, the entire contents of which are incorporated herein by reference.

BACKGROUND OF THE INVENTION

1. Field of the Invention

The present invention relates to a pattern inspection apparatus and a pattern inspection method. For example, it relates to an inspection apparatus that inspects a pattern based on an optical image of a pattern image acquired by using an illumination light and to a method thereof.

2. Description of Related Art

In recent years, with high integration and large capacity of large scale integrated (LSI) circuits, the line width (critical dimension) required for circuits of a semiconductor element is becoming narrower and narrower. Such a semiconductor element is manufactured by exposing (transferring) a pattern onto a wafer to form a circuit by a reduced projection exposure apparatus, known as a stepper, by using an original or "master" pattern with a circuit pattern formed thereon. The original pattern is also called a mask or a reticle, and hereinafter generically referred to as a mask. Therefore, in manufacturing a mask for transferring such a fine circuit pattern onto a wafer, a pattern writing apparatus using electron beams capable of writing or "drawing" fine circuit patterns needs to be employed. Pattern circuits may be written directly onto a wafer by the pattern writing apparatus. In addition to the writing apparatus using electron beams, a laser beam writing apparatus which uses laser beams for writing patterns is also under development.

Since the LSI manufacturing requires a tremendous amount of manufacturing cost, it is crucial to improve its yield. However, as represented by a 1 gigabit DRAM (Dynamic Random Access Memory), the order of a pattern constituting an LSI has been changing from submicron to nanometer dimensions. One of major factors that decrease the yield of the LSI manufacturing is a pattern defect of a mask used when exposing (transferring) a fine pattern onto a semiconductor wafer by the photolithography technology. In recent years, with miniaturization of an LSI pattern formed on a semiconductor wafer, dimensions to be detected as a pattern defect have become extremely small. Thus, a pattern inspection apparatus for inspecting defects of a mask for exposure used in manufacturing LSI needs to be highly accurate.

Meanwhile, with development of multimedia technology, the size of LCD (Liquid Crystal Display) substrates is becoming larger, e.g., 500 mm×600 mm or greater, and the size of a pattern such as a TFT (Thin Film Transistor) or the like formed on the liquid crystal substrate is becoming finer. Therefore, it is increasingly required that an extremely small defect of a pattern should be inspected in a large range. For this reason, development of a pattern inspection apparatus that efficiently and short-timely inspects a defect of a pattern of a large area LCD and a defect of a photo mask used in manufacturing the large area LCD is urgently required.

As inspection methods, it is known that an optical image of a pattern formed on a target object or "sample", such as a lithography mask, imaged at a predetermined magnification using a magnifying optical system is compared with design data, or that optical images of identical patterns on the target object are compared. For example, the following is known as pattern inspection methods: die-to-die inspection method that compares data of optical images of identical patterns at different positions on the same mask, and die-to-database inspection method that inputs, into the inspection apparatus, writing data (design pattern data) which is generated by converting pattern-designed CAD data to an appropriate format to be input into the writing apparatus when writing a pattern on a mask, generates design image data (reference image) based on the input writing data, and compares the generated design image data with an optical image (serving as measured data) obtained by imaging the pattern. According to the inspection method of the inspection apparatus, a target object is placed on the stage so that a light flux may scan the object by the movement of the stage in order to perform an inspection. Specifically, the target object is irradiated with a light flux from the light source and the illumination optical system. Light transmitted through the target object or reflected therefrom is focused on a sensor through the optical system. An image captured by the sensor is transmitted as measured data to the comparison circuit. In the comparison circuit, after position alignment of the images, measured data and reference data are compared in accordance with an appropriate algorithm. If there is no matching between the data, it is judged that a pattern defect exists.

Laser light is used for performing the pattern inspection described above. Laser light generated and emitted from the light source is divided by using an integrator lens, and then, the divided lights illuminate, in an overlapping manner, the surface of the target object by an optical system such as a condenser lens. However, in such a configuration, illumination intensities at a plurality of focal points formed by the integrator lens are high, which causes a problem of degrading optical elements arranged near the focal points.

Although not related to a pattern inspection apparatus, there is disclosed a device for detecting the height of a target object, where an illumination optical system that divides a laser light by using an integrator lens is mounted (refer to, e.g., Japanese Patent Application Laid-open (JP-A) No. 2011-053120).

BRIEF SUMMARY OF THE INVENTION

In accordance with one aspect of the present invention, a pattern inspection apparatus includes a laser light source configured to emit a laser light, an integrator lens configured to input the laser light, and form a light source group by dividing the laser light inputted, a scattering plate, arranged at a front side of an incident surface of the integrator lens, configured to scatter the laser light which is to enter the integrator lens, and an inspection unit configured to inspect a defect of a pattern on an inspection target object where a plurality of figure patterns are formed, by using the laser light having passed through the integrator lens as an illumination light.

In accordance with another aspect of the present invention, a pattern inspection method includes emitting a laser light from a laser light source, scattering the laser light, which is to enter an integrator lens, by letting the laser light pass through a scattering plate arranged at a front side of an incident surface of an integrator lens that forms a light source group by dividing the laser light, inputting a scattered laser light into the integrator lens and dividing an input laser light to form the light source group, and inspecting a defect of a pattern on an inspection target object where a plurality of figure patterns are formed, by using the laser light having passed through the integrator lens as an illumination light.

DETAILED DESCRIPTION OF THE INVENTION

Embodiment 1

As described above, since illumination intensities at a plurality of focal points formed by an integrator lens are high, there is a problem in that optical elements arranged near the focal points are degraded. A sufficient method for solving this problem has not been established yet.

Hereafter, in Embodiment 1, there will be described an inspection apparatus and a method thereof that can avoid the degradation (damage) of optical elements resulting from a plurality of focal points formed by an integrator lens.

Figure 1:
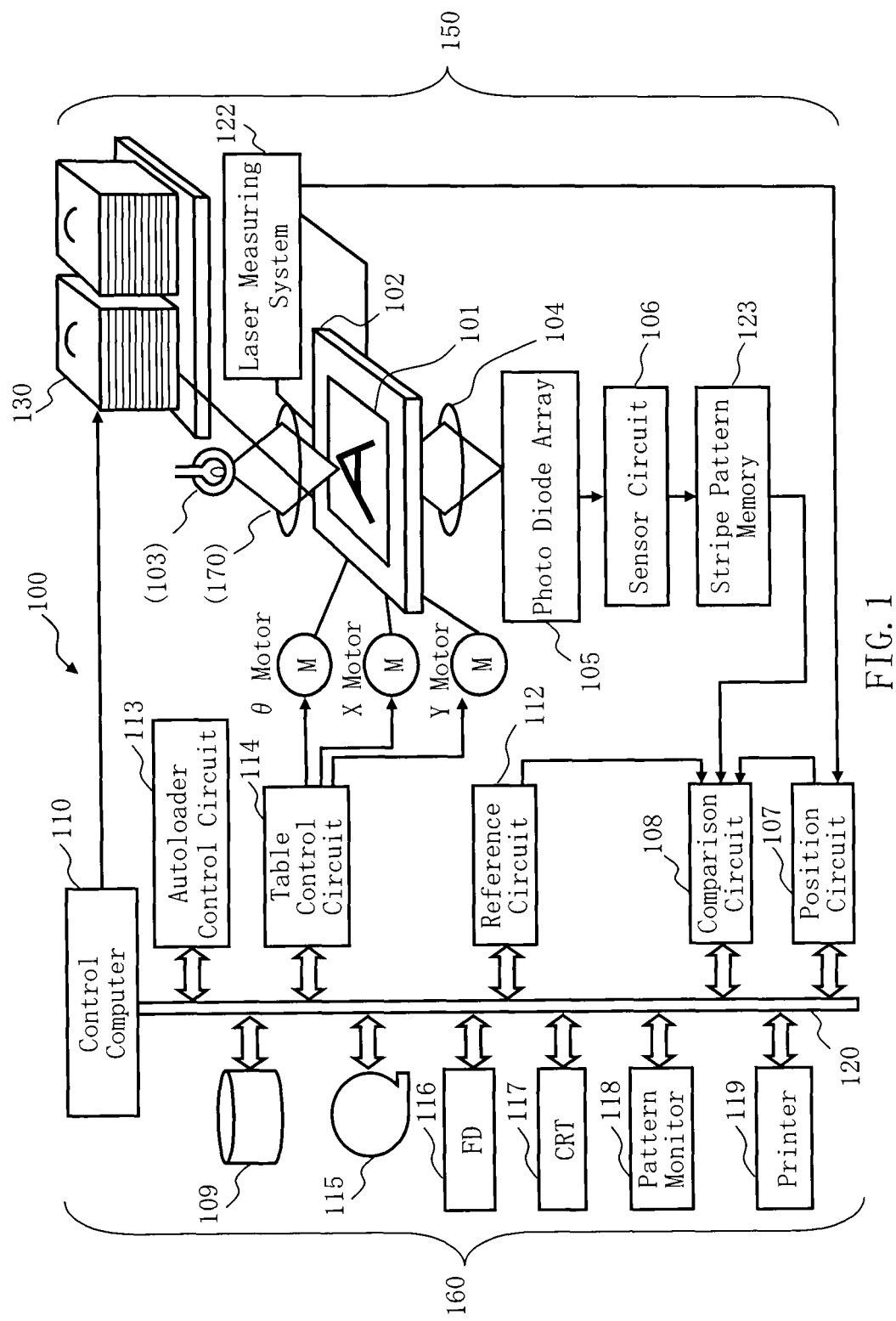
FIG. 1 is a schematic diagram showing a configuration of a pattern inspection apparatus according to Embodiment 1.

FIG. 1 is a schematic diagram showing a configuration of a pattern inspection apparatus according to Embodiment 1. In FIG. 1, an inspection apparatus 100 for inspecting a defect of a target object, such as a mask, includes a light source 103, an illumination optical system 170, an inspection unit 150, and a control system circuit 160. The inspection unit 150 includes an XYθ table 102, a magnifying optical system 104, a photo diode array 105 (an example of a sensor), a sensor circuit 106, a stripe pattern memory 123, a laser measuring system 122, and an autoloader 130. In the control system circuit 160, a control computer 110 is connected, through a bus 120, to a position circuit 107, a comparison circuit 108, a reference circuit 112, an autoloader control circuit 113, a table control circuit 114, a magnetic disk drive 109, a magnetic tape drive 115, a flexible disk drive (FD) 116, a CRT 117, a pattern monitor 118, and a printer 119. The sensor circuit 106 is connected to the stripe pattern memory 123 which is connected to the comparison circuit 108. The XYθ table 102 is driven by an X-axis motor, a Y-axis motor, and a θ-axis motor. The XYθ table 102 serves as an example of the stage. FIG. 1 shows structure elements necessary for describing Embodiment 1, and it should be understood that other structure elements generally necessary for the inspection apparatus 100 may also be included therein.

In the inspection apparatus 100, an inspection optical system of large magnification is composed of the light source 103, the XYθ table 102, the illumination optical system 170, the magnifying optical system 104, the photo diode array 105, and the sensor circuit 106. The XYθ table 102 is driven by the table control circuit 114 under the control of the control computer 110. The XYθ table 102 can be moved by a drive system such as a three-axis (X, Y, and θ) motor, which drives the XYθ table 102 in the X direction, the Y direction, and the θ direction. For example, a step motor can be used as each of these X, Y, and θ motors. The moving position of the XYθ table 102 is measured by the laser measuring system 122 and supplied to the position circuit 107. A photo mask 101 on the XYθ table 102 is automatically conveyed from the autoloader 130 which is driven by the autoloader control circuit 113, and automatically ejected after the inspection.

The photo mask 101 serving as an inspection target object, on which a plurality of figure patterns are formed, is placed on the XYθ table 102 that is movable in a horizontal direction and a rotating direction by the X-, Y-, and θ-axis motors. Then, the patterns written on the photo mask 101 are irradiated by a light (inspection light) of a wavelength of, or below, the ultraviolet region emitted from the suitable light source 103 through the illumination optical system 170. The light transmitted through the photo mask 101 is focused on the photo diode array 105, via the magnifying optical system 104, as an optical image and enters thereinto. It is preferable to use, for example, a TDI (Time Delay Integration) sensor as the photo diode array 105.

Figure 2:
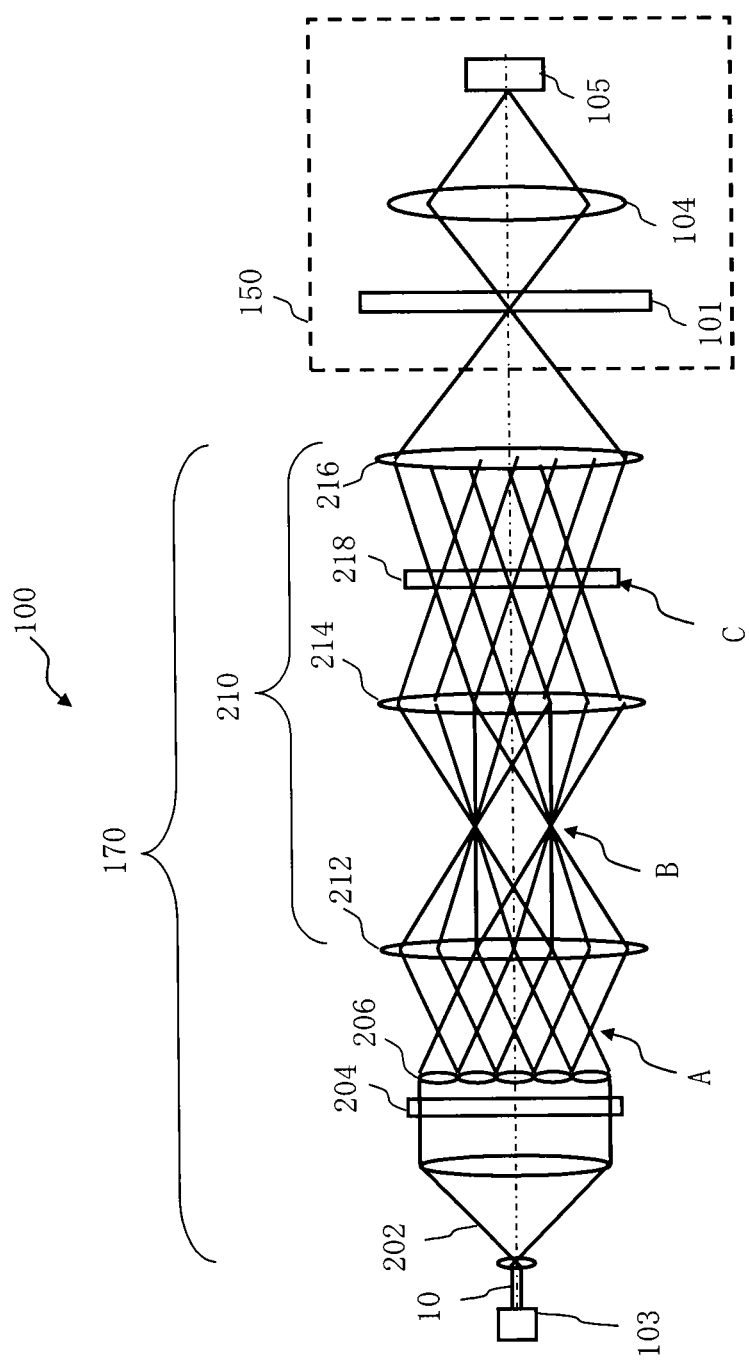
FIG. 2 is a configuration diagram showing an example of the configuration of an illumination optical system according to Embodiment 1.

FIG. 2 is a configuration diagram showing an example of the configuration of an illumination optical system according to Embodiment 1. In FIG. 2, the illumination optical system 170 includes a beam expander (expander lens) 202, a scattering plate 204, an integrator lens (dividing lens) 206, a lens group 210, and an optical element 218. The lens group 210 includes lenses 212, 214, and 216. Although an example of the lens group 210 composed of three lenses 212, 214, and 216 is shown in this case, it is not limited thereto. It is also acceptable to transmit the illumination light to the inspection unit 150 through other optical elements. The scattering plate 204 is arranged at the front side of the incident surface of the integrator lens 206.

The light source 103 used as a laser light source generates and emits a laser light 10. The laser light 10 emitted from the light source 103 is expanded by the beam expander 202. The laser light 10 having passed through the beam expander 202 is scattered, by the scattering plate 204, to enter the integrator lens 206. The laser light 10 passes through a region including the center of the surface of the scattering plate 204. By letting the laser light 10 pass through the region including the center of the surface of the scattering plate 204, the surface of the scattering plate 204 can be effectively utilized. The material of the scattering plate 204 is required to let the light pass, and it is more preferable to be a material that is transparent as much as possible and does not absorb the light. Decrease in the light quantity of the laser light 10 can be reduced by making the transmission rate high as much as possible. For example, a glass material, etc. is desirable.

The scattered laser light 10 enters the integrator lens 206 and is divided to form a light source group (a plurality of light sources). Light beams spread from the light source group formed by the integrator lens 206 pass through the lens group 210, and are overlapped on the surface of the photo mask 101 used as a target object in the inspection unit 150. Lights from the light source group formed by the integrator lens 206 are condensed or "collected" on a plane A (a first plane or a light condensing surface) before entering the lens group 210. Then, they are condensed on a plane C (a second plane or a light condensing surface), which is a conjugate plane of the plane A, between the objective lenses in the lens group 210. A plane B serves as a conjugate plane of the surface of the photo mask 101, for example. The optical element 218 is arranged near the plane C, and specifically, arranged within a range of a predetermined distance from the position of the plane C. The range of a predetermined distance is, for example, a range where, in the case of not using the scattering plate 204, the energy obtained by the illumination intensity (illuminance) of the light source group illuminating the optical element 218 damages the optical element 218.

Figure 3:
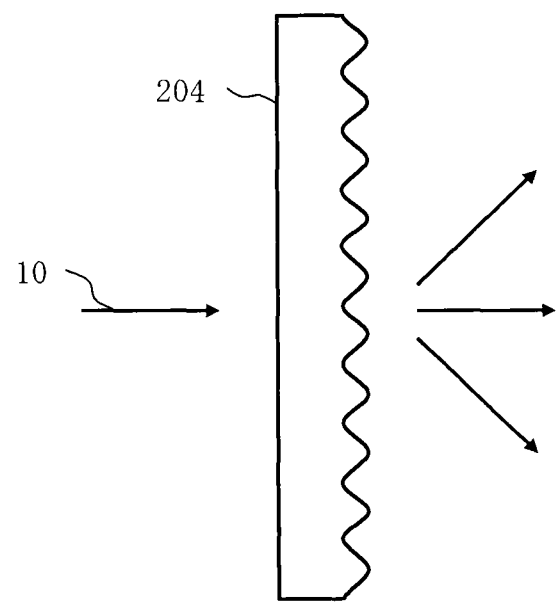
FIG. 3 shows an example of the structure of a scattering plate according to Embodiment 1.

FIG. 3 shows an example of the structure of the scattering plate according to Embodiment 1. The incident surface or the light emitting surface of the scattering plate 204 in FIG. 3 is formed in concave and convex surface. Therefore, the scattering plate 204 can scatteringly emit the passing laser light 10.

Figure 4A:
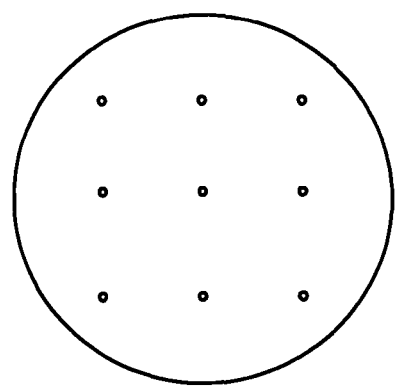
FIGS. 4A and 4B show examples of the shape of a light source group at focal points according to Embodiment 1.
Figure 4A:
Figure 4B:
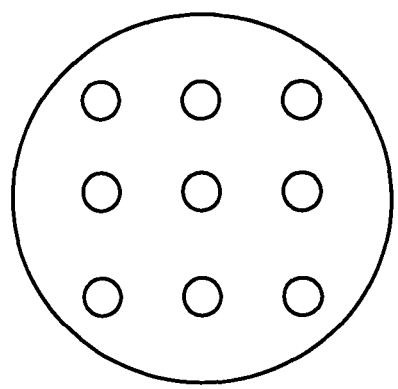

FIGS. 4A and 4B show examples of the shape of the light source group at the planes A and C according to Embodiment 1. When the laser light 10 enters the integrator lens 206 in the state where the scattering plate 204 is not arranged, a point light source group is formed as shown in FIG. 4A. Then, since the light is collected at each point, the illumination intensity of each point light source is too high. Therefore, if the light source group is focused by the lenses 212, 214, etc., the optical element 218 arranged near the focal point position is irradiated by the light having a too high illumination intensity, thereby deteriorating the optical element 218. On the other hand, according to Embodiment 1, since the scattering plate 204 is arranged at the front side of the integrator lens 206, the laser light 10 to enter the integrator lens 206 can be scattered. Therefore, the light source group formed bypassing through the integrator lens 206 can be a surface instead of a point, as shown in FIG. 4B. In other words, it can be blurred. Accordingly, since the illumination intensity can be dispersed from the point to the surface, an illumination intensity acting on one point can be made low. That is, by scattering a laser light by using the scattering plate 204, compared with the case of no scattering without the scattering plate 204, the illumination intensity (strength per unit area) of light from the light source group, which is formed by passing through the integrator lens 206, at the surface where lights from the light source group are collected can be controlled to be small. As a result, even if the light source group is focused by the lenses 212 and 214, the illumination intensity of the light illuminating the optical element 218 arranged near the focal point position can be reduced. Then, degradation (damage) of the optical element 218 can be inhibited or reduced. As the optical element 218, it is preferable to use, for instance, a polarization element, a diffraction element, or a diaphragm. For example, a Wollaston prism is used in a differentiation interference optical system.

Moreover, since the scattering plate 204 is arranged at the front side of the incident surface of the integrator lens 206, the illumination unevenness caused by the scattering plate 204 is divided by the integrator lens, to overlap each other on the mask surface. Thereby, the unevenness of the illumination intensity is equalized not to directly affect the unevenness of the light quantity on the surface of the photo mask 101.

Figure 5:
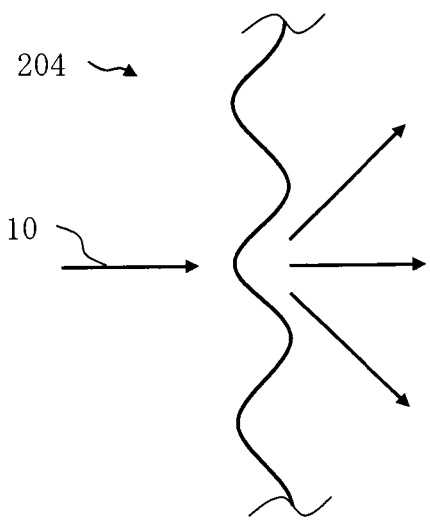
FIG. 5 shows an example of the structure of the surface of the scattering plate according to Embodiment 1.

FIG. 5 shows an example of the structure of the surface of the scattering plate according to Embodiment 1. The surface of the scattering plate 204 of FIG. 5 is formed by a curved surface. By virtue of this structure, the incident light can be scattered. However, the structure of the surface of the scattering plate is not limited thereto.

Figure 6:
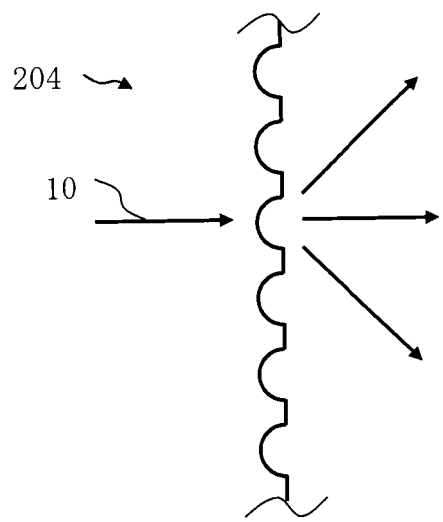
FIG. 6 shows another example of the structure of the surface of the scattering plate according to Embodiment 1.

FIG. 6 shows another example of the structure of the surface of the scattering plate according to Embodiment 1. The surface of the scattering plate 204 of FIG. 6 is formed by a combination of curved surfaces and planes. Also, in this structure, the incident light can be scattered.

Figure 7:
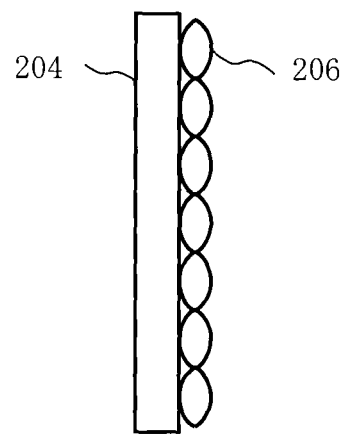
FIG. 7 shows a modified example of the arrangement position of the scattering plate according to Embodiment 1.

FIG. 7 shows a modified example of the arrangement position of the scattering plate according to Embodiment 1. The scattering plate 204 in FIG. 2 is arranged near the incident surface of the integrator lens 206 and keeps space to the integrator lens 206, namely not contacting, but it is not limited thereto. It is also preferable to arrange the scattering plate 204 shown in FIG. 3, 5, or 6 such that it contacts with the integrator 206 as shown in FIG. 7. Thereby, the light scattered by the scattering plate 204 can be controlled from leaking to the circumference without entering the integrator lens 206.

Figure 8:
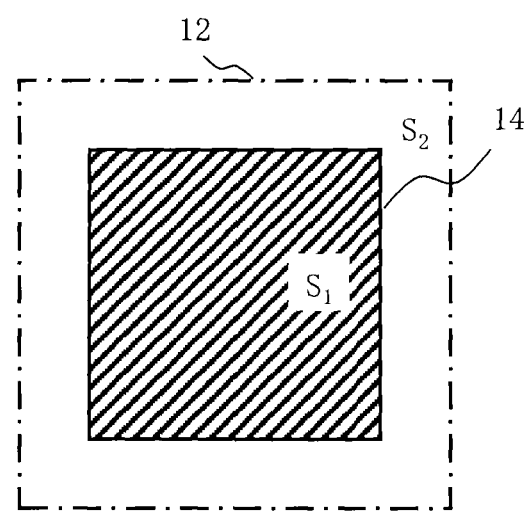
FIG. 8 is a schematic diagram showing an example of the size of a light after passing through the scattering plate and the size of a light to enter the integrator lens according to Embodiment 1.

FIG. 8 is a schematic diagram showing an example of the size of a light after passing through the scattering plate and the size of a light to enter the integrator lens. In Embodiment 1, it is desirable for an area S2 of the section of a light 12 which has passed through the scattering plate 204 to be, for example, less than or equal to 110% of an area S1 of the section of a light 14 which is to enter the integrator lens 206. Thereby, the decrease in the light quantity, caused by passing through the scattering plate 204, can be controlled to be, for example, less than or equal to 10% of the allowable rate of decrease in the light quantity of the illumination light used for the inspection apparatus 100. As a result, degradation of measured images due to a light quantity decrease can be inhibited. That is, it is preferable that the area S2 of the section of the light 12 which has passed through the scattering plate 204 is controlled to be within a value obtained by adding the allowable rate of decrease in the light quantity of the illumination light used for the inspection apparatus 100 to the area S1 of the section of the light 14 which is to enter the integrator lens 206. Therefore, it is preferable for the positional relationship between the scattering plate 204 and the integrator lens 206 to be suitably adjusted in view of the above.

As described above, according to Embodiment 1, each illumination intensity of a plurality of focal points formed by the integrator lens 206 can be made low. Thus, even when an optical element is arranged near the focal point, degradation of the optical element can be avoided.

Figure 9:
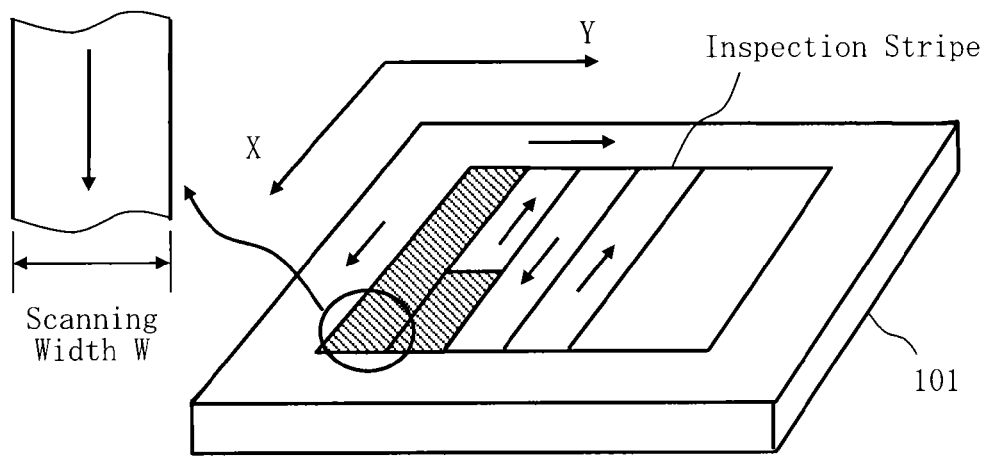
FIG. 9 is a schematic diagram describing a procedure for acquiring an optical image according to Embodiment 1.

FIG. 9 is a schematic diagram describing a procedure for acquiring an optical image according to Embodiment 1. An inspection region is virtually divided into a plurality of strip-like inspection stripes (an example of a small region or a stripe region) each having a scanning width W in the Y direction, for example. The operation of the XYθ table 102 is controlled such that each divided inspection stripe is scanned continuously. By the movement of the XYθ table 102, optical images are acquired by the photo diode array 105 which moves relatively in the X direction continuously. That is, the photo diode array 105 continuously captures optical images each having a scanning width W as shown in FIG. 9. In other words, the photo diode array 105, being an example of a sensor, captures optical images of a plurality of figure patterns formed on the photo mask 101 by using an inspection light, while moving relatively to the movement of the XYθ table 102 (stage). According to Embodiment 1, after capturing an optical image in one inspection stripe, the photo diode array 105 similarly captures another optical image having the scanning width W continuously at a position shifted in the Y direction by a scanning width W, while moving in a direction reverse to the last image capturing direction. That is, the image capturing is repeated in the forward (FWD) and backward (BWD) directions, meaning going in a reverse direction when advancing and returning.

Then, the direction of the image capturing is not limited to repeating the forward (FWD) and the backward (BWD) movement. It is also acceptable to capture an image from one direction with respect to each inspection stripe 20. For example, repeating a FWD-FWD movement may be sufficient, and alternatively, a BWD-BWD movement may also be sufficient.

The pattern image focused on the photo diode array 105 is photoelectrically converted by each light receiving element of the photo diode array 105, and further analog-to-digital (A/D) converted by the sensor circuit 106. Pixel data of each inspection stripe is stored in the stripe pattern memory 123. Then, the pixel data is sent to the comparison circuit 108, with data which is output from the position circuit 107 and indicates the position of the photo mask 101 on the XYθ table 102. Measured data is 8-bit unsigned data, for example, and indicates a gray level (light intensity or light quantity) of brightness of each pixel.

On the other hand, in a reference image generation step, the reference circuit 112 reads design data with respect to each inspection stripe in order from the magnetic disk drive 109 through the control computer 110. Then, the read design data of the photo mask 101 is converted into image data of binary values or multiple values in order to generate reference data (reference image). The reference data is 8-bit unsigned data, for example, and indicates a gray level (light intensity or light quantity) of brightness of each pixel. The reference data is sent to the comparison circuit 108.

In a comparison step, the comparison circuit 108 (inspection unit) inputs measured data (optical image), for each inspection stripe, from the stripe pattern memory 123, and inputs reference data (reference image) from the reference circuit 112.

Then, position alignment is performed between the measured data and the reference data. Each pixel data of the measured data and reference pixel data of the reference data are compared, for each pixel, according to a predetermined algorithm, and existence of a defect is judged based on the comparison result. For example, it is judged by checking whether the difference between pixel values of the measured data and the reference data is less than or equal to a threshold value or not. Then, the comparison result is output, for example, to the magnetic disk drive 109, the magnetic tape drive 115, the FD 116, the CRT 117, the pattern monitor 118, or the printer 119. Alternatively, it may be output to the outside.

As described above, the inspection unit 150 inspects a defect of a pattern on the photo mask 101 (inspection target object) where a plurality of figure patterns are formed, by using a laser light having passed through the integrator lens 206 as an illumination light.

Figure 10:
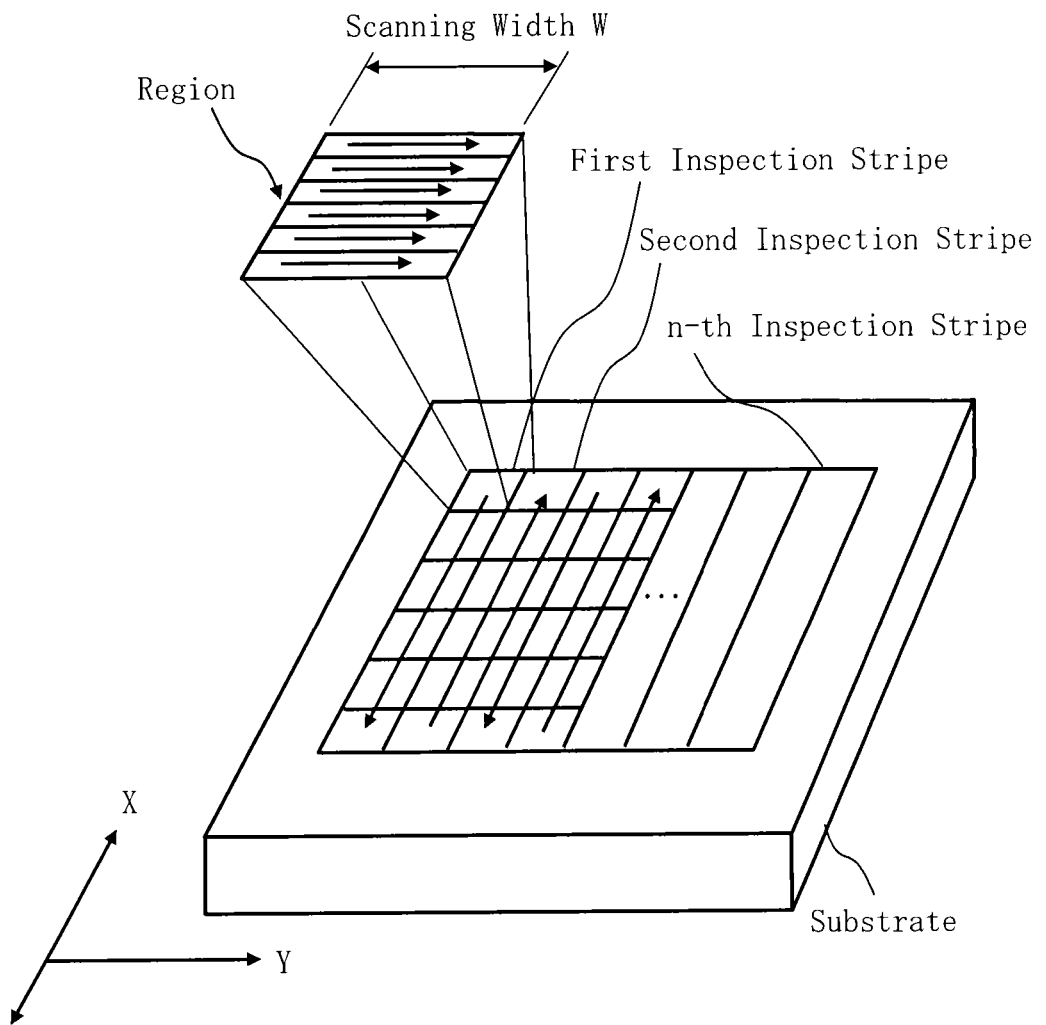
FIG. 10 shows another method for acquiring an optical image.

FIG. 10 shows another method for acquiring an optical image. With the configuration of FIG. 1, the photodiode array 105 which simultaneously inputs beams corresponding to the number of pixels (for example, 2048 pixels) of the scanning width W is employed, but not limited thereto. As shown in FIG. 10, an alternative method may be used in which, while the XYθ table 102 is moved at a constant speed in the X direction, a laser scanning optical device (not shown) scans with a laser beam in the Y direction at every time detecting a movement of a specific pitch by a laser interferometer, and acquires a two-dimensional image in every region of a predetermined size by way of detecting transmitted lights.

As described above, according to the present Embodiment, each illumination intensity of a plurality of focal points formed by an integrator lens can be made low. Therefore, even when an optical element is arranged near the focal point, degradation of the optical element can be avoided.

In the above description, processing contents or operation contents of what is expressed by the term "circuit" or "step" can be configured by hardware such as an electronic circuit etc. or by a computer operable program. Alternatively, they may be implemented not only by a program being software but also by a combination of hardware and software, or further, by a combination of hardware and firmware. When configured by a program, the program is stored in a computer readable recording medium, such as a magnetic disk drive, a magnetic tape drive, FD, or ROM (Read Only Memory). For example, the table control circuit 114, the reference circuit 112, the reference circuit 142, the comparison circuit 108, etc. which constitute the operation control unit may be configured by an electric circuit. Alternatively, they may be implemented as software to be processed by the control computer 110, or implemented by a combination of electric circuits and software.

Referring to specific examples, Embodiments have been described above. However, the present invention is not limited to these examples. For example, the transmission illumination optical system which uses a transmitted light is described as an illumination optical system 170 in the Embodiment, but it is not limited thereto. For example, it may be a reflection illumination optical system which uses a reflected light. Alternatively, it is also acceptable to simultaneously use a transmitted light and a reflected light by combining the transmission illumination optical system and the reflection illumination optical system. Moreover, a die-to-database inspection that compares measured data with a reference image generated from design data is performed in the Embodiment, but it is not limited thereto. It is also acceptable to perform a die-to-die inspection that compares measured data each other by using the photo mask where identical patterns are formed.

While the apparatus configuration, control method, etc. not directly necessary for explaining the present invention are not described, some or all of them may be suitably selected and used when needed. For example, although description of the configuration of a control unit for controlling the writing apparatus 100 is omitted, it should be understood that some or all of the configuration of the control unit is to be selected and used appropriately when necessary.

In addition, any other pattern inspection apparatus and a method thereof that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus comprising:
   a laser light source configured to emit a laser light;
   an integrator lens configured to input the laser light, and form a light source group by dividing the laser light inputted;
   a scattering plate, arranged between the integrator lens and the laser light source, configured to scatter the laser light which is to enter the integrator lens; and
   an inspection unit configured to inspect a defect of a pattern on an inspection target object where a plurality of figure patterns are formed, by using the laser light having passed through the integrator lens as an illumination light.

2. The apparatus according to claim 1,
wherein a surface of the scattering plate is formed by one of a curved surface and a combination of a curved surface and a plane.

3. The apparatus according to claim 1,
wherein the scattering plate is arranged in direct contact with the integrator lens.

4. The apparatus according to claim 1,
wherein the laser light passes through a region including a center of a surface of the scattering plate.

5. The apparatus according to claim 1,
wherein an area of a section of the laser light which has passed through the scattering plate is controlled to be within a value obtained by adding an allowable rate of decrease in a light quantity of an illumination light used for the pattern inspection apparatus to an area of a section of the laser light which is to enter the integrator lens.

6. The apparatus according to claim 1, further comprising:
a lens group, arranged at a light emitting surface side of the integrator lens, configured to condense laser lights from the light source group formed by the integrator lens.

7. The apparatus according to claim 6,
wherein the laser lights from the light source group formed by the integrator lens are condensed on a first plane before entering the lens group.

8. The apparatus according to claim 7,
wherein the laser lights from the light source group are condensed on a second plane, which is a conjugate plane of the first plane, by the lens group.

9. The apparatus according to claim 8, further comprising:
an optical element arranged within a range of a predetermined distance from a position of the second plane.

10. The apparatus according to claim 9,
wherein the range of the predetermined distance is a range where, in a case of not using the scattering plate, an illumination intensity of the light source group illuminating the optical element damages the optical element.

11. The apparatus according to claim 1,
wherein an illumination intensity of the laser light from the light source group, which is formed by passing through the integrator lens, at a surface where laser lights from the light source group are condensed is controlled to be small by scattering the laser light by using the scattering plate, compared with a case of no scattering without the scattering plate.

12. A pattern inspection method comprising:
emitting a laser light from a laser light source;
scattering the laser light, which is to enter an integrator lens, by letting the laser light pass through a scattering plate arranged between an integrator lens that forms a light source group by dividing the laser light, and the laser light source;
inputting a scattered laser light into the integrator lens and dividing an input laser light to form the light source group; and
inspecting a defect of a pattern on an inspection target object where a plurality of figure patterns are formed, by using the laser light having passed through the integrator lens as an illumination light.

13. The method according to claim 12,
wherein the scattering plate whose surface is formed by one of a curved surface and a combination of a curved surface and a plane is used.

14. The method according to claim 12,
wherein the scattering plate is arranged in direct contact with the integrator lens.

15. The method according to claim 12,
wherein the laser light passes through a region including a center of a surface of the scattering plate.

16. The method according to claim 12,
wherein an area of a section of the laser light which has passed through the scattering plate is controlled to be within a value obtained by adding an allowable rate of decrease in a light quantity of an illumination light used for the pattern inspection apparatus to an area of a section of the laser light which is to enter the integrator lens.

17. The method according to claim 12, further comprising:
condensing laser lights from the light source group formed by the integrator lens, by using a lens group arranged at a light emitting surface side of the integrator lens.

18. The method according to claim 17,
wherein the laser lights from the light source group formed by the integrator lens are condensed on a first plane before entering the lens group.

19. The method according to claim 18,
wherein the laser lights from the light source group are condensed on a second plane, which is a conjugate plane of the first plane, by the lens group.

20. The method according to claim 12,
wherein an illumination intensity of the laser light from the light source group, which is formed by passing through the integrator lens, at a surface where laser lights from the light source group are condensed is controlled to be small by scattering the laser light by using the scattering plate, compared with a case of no scattering without the scattering plate.

* * * * *